(12) United States Patent
Resnick

(10) Patent No.: US 7,406,154 B2
(45) Date of Patent: Jul. 29, 2008

(54) HIGH SPEED MODULATION OF SWITCHED-FOCUS X-RAY TUBE

(75) Inventor: Theodore A Resnick, Beachwood, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 293 days.

(21) Appl. No.: 10/541,563

(22) PCT Filed: Jan. 5, 2004

(86) PCT No.: PCT/IB2004/000007

§ 371 (c)(1),
(2), (4) Date: Jul. 6, 2005

(87) PCT Pub. No.: WO2004/061864

PCT Pub. Date: Jul. 22, 2004

(65) Prior Publication Data

US 2006/0115050 A1      Jun. 1, 2006

Related U.S. Application Data

(60) Provisional application No. 60/438,216, filed on Jan. 6, 2003.

(51) Int. Cl.
*H05G 1/44* (2006.01)
(52) U.S. Cl. .................. 378/113; 378/138
(58) Field of Classification Search ......... 378/137–138, 378/108–113, 119, 122, 136, 4
See application file for complete search history.

(56) References Cited

U.S. PATENT DOCUMENTS

| 4,051,377 | A |   | 9/1977  | Kemner et al.            |
|-----------|---|---|---------|--------------------------|
| 4,189,641 | A |   | 2/1980  | Katagiri et al.          |
| 4,703,496 | A |   | 10/1987 | Meccariello et al.       |
| 5,065,420 | A |   | 11/1991 | Levene                   |
| 5,550,889 | A | * | 8/1996  | Gard et al. ....... 378/113 |
| 5,621,781 | A | * | 4/1997  | Blake et al. ...... 378/138 |
| 5,748,701 | A | * | 5/1998  | Mika et al. ....... 378/109 |
| 5,822,393 | A |   | 10/1998 | Popescu                  |
| 5,867,555 | A |   | 2/1999  | Popescu et al.           |
| 6,111,933 | A | * | 8/2000  | Schaaf et al. ..... 378/137 |
| 6,256,369 | B1 |  | 7/2001  | Lai                      |
| 6,385,280 | B1 |  | 5/2002  | Bittl et al.             |

OTHER PUBLICATIONS

Varian Medical Systems; X-Ray Products GS1596; CT Scanner X-Ray Tube; 5012; Rev. 1; Apr. 2000; 6 pp.

* cited by examiner

*Primary Examiner*—Hoon Song

(57) ABSTRACT

A dose-modulated irradiating system includes an x-ray tube (20) with at least a filament (80) for generating electrons, a cathode (84) and an anode (92) for accelerating and collimating the generated electrons into an electron beam (94), and an electrostatic grid with grid electrodes (110, 112) for steering the electron beam (94) on the anode (92). The anode (92) generates an x-ray beam (96) responsive to the electron beam (94). Grid biasing is provided for applying a time-varying electrical bias to the grid electrodes (110, 112) that produces a first time-varying intensity modulation of the electron beam (94). A current of the filament (80) is modulated to produce a second time-varying intensity modulation of the electron beam (94). A controller (52) controls cooperatively combining the first and second time-varying intensity modulations to produce a combined time-varying intensity modulation.

26 Claims, 3 Drawing Sheets

HIGH SPEED MODULATION OF SWITCHED-FOCUS X-RAY TUBE

CROSS REFERENCE TO RELATED APPLICATIONS

Figure 1:
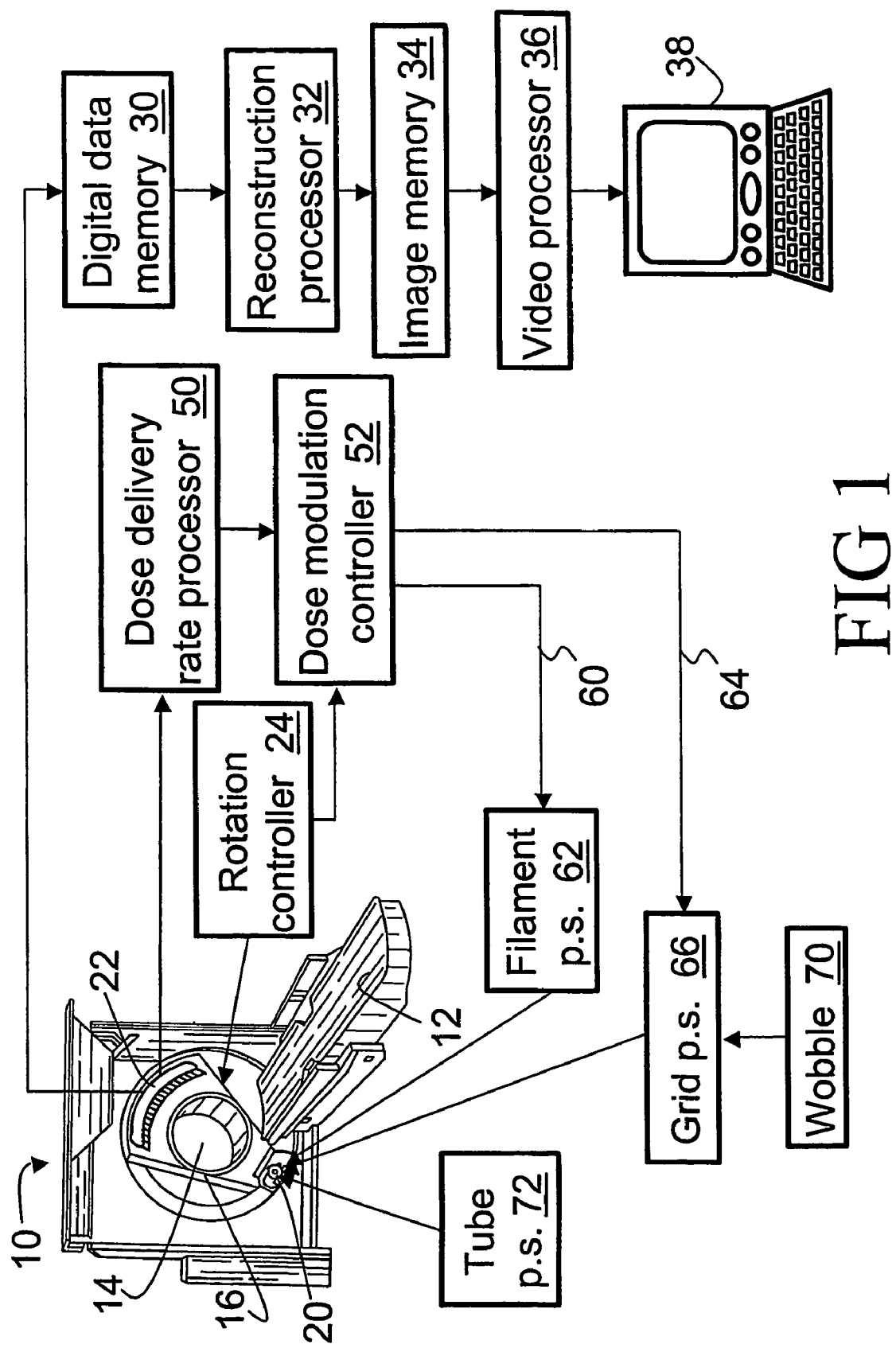

This application claims the benefit of U.S. Provisional Application Ser. No. 60/438,216 filed Jan. 6, 2003, which is incorporated herein by reference.

The following relates to the diagnostic imaging arts. It finds particular application in conjunction with dose-modulation by cascading frequency responses of x-ray tube filament current and grid voltage for computed tomography imaging, and will be described with particular reference thereto. However, the following relates more generally to dose-modulated and other types of computed tomography imaging and to x-ray tubes used in other applications.

In a typical computed tomography imaging apparatus, an x-ray tube is mounted on a rotating gantry that defines an examination region inside which an imaging subject is disposed. The x-ray tube rotates about the subject on the rotating gantry and projects a wedge-, fan-, conical-, or otherwise-shaped x-ray beam through the examination region. A two-dimensional x-ray detector disposed on the rotating gantry across the examination region from the x-ray tube receives x-ray beam after passing through the examination region. Suitable electronics estimate x-ray absorption data based on the detected x-ray intensities, and an image reconstruction processor reconstructs an image representation based on the absorption data.

The x-ray tube in the above arrangement typically includes a filament that generates electrons. A cathode cup partially surrounds the filament and is biased negatively to focus the electrons into an electron beam. A bias in the kilovolt range between the cup and a rotating anode accelerates the electron beam to the anode, causing it to emit x-rays.

A problem arises in that the imaging data is under-sampled in the rotational direction. Sampling occurs at a spatial frequency related to the detector spacing, while sampling theory calls for a doubled spatial frequency to avoid aliasing and other sampling-related artifacts. To counteract under-sampling, an x-ray tube is employed in which the focal spot is alternated or wobbled between two discrete positions in the rotational direction between measurements to spatially inter-leave samples. Alternatively, a quarter ray offset can be employed in which rays from opposing 180° projection views are spatially interleaved.

To effect beam wobble, the x-ray tube includes grid electrodes arranged on opposite sides of the filament. The grid electrodes are biased with an alternating polarity to generate a switched electrostatic force orthogonal to the electron beam that shifts the electron beam between two paths corresponding to the two focal spots of the wobble. Alternatively, an orthogonal electromagnetic force can be used to switchingly steer the beam.

Another concern in computed tomography imaging is limiting x-ray exposure of the subject. In medical imaging applications, the x-ray dosage delivered to the patient is a regulated safety parameter. In airport security scanning, the x-ray intensity is advantageously adjusted to account for differing x-ray absorption characteristics of different types of luggage. Various dose-modulated computed tomography techniques have been developed. However, these past methods have certain disadvantages.

In one method, described in U.S. Pat. No. 5,867,555 issued to Popescu et al., dose modulation as a function of angular position is obtained by synchronously modulating the x-ray tube filament temperature. As noted in that reference, however, the modulation index obtained by filament current control is limited by a cooling rate (thermal mass) of the filament, especially at higher rotation speeds. The Popescu technique changes the dose once every 180° in a scanner that rotates once every 0.75-2.0 seconds, which pushes the limit of the filaments ability to respond. Thermal mass limitations are also exaggerated for higher dynamic modulation ranges which involve substantial cooling of the filament. The cooling rate decreases as the temperature decreases.

Modern scanners rotate twice per second and faster speeds are starting to appear in product. Moreover, more dose changes per revolution are advantageous, setting modulation speeds that exceed the physical limits of the Popescu technique.

In another known method, a Wehnelt cylinder incorporated into the x-ray tube selectively pinches off the beam to switch the beam on and off. Beam switching is synchronized with a CINE frame sequence to dose-modulate by controlling a duty cycle of the x-ray beam. However, this dose modulation approach reduces the amount of collected angular data.

The present invention contemplates an improved apparatus and method that overcomes the aforementioned limitations and others.

According to one aspect, a dose-modulated irradiating system for an x-ray tube is disclosed. The x-ray tube has a cathode including a filament that generates electrons which are focused into a beam, and an anode that generates x-rays responsive to the electron beam. At least one electrostatic control electrode is arranged to electrostatically reduce an intensity of the electron beam. A biasing means is provided for applying a time-varying electrical bias to the electrostatic control electrode to vary the intensity of the electron beam.

According to another aspect, a method is provided for dose-modulating an output of an x-ray tube. The x-ray tube includes a cathode having a filament that generates electrons which are focused into a beam, an anode that generates x-rays responsive to the electron beam, and an electrostatic control electrode that electrostatically adjusts an intensity of the electron beam. A time-varying electrical bias is applied to the electrostatic control electrode to produce a first time-varying intensity modulation of the electron beam.

One advantage resides in providing a high dynamic range of dose modulation at a high modulation frequency. This facilitates dose modulation using present- and next-generation computed tomography scanners which rotate at rates of 120 rpm or higher.

Another advantage resides in providing such dose modulation without modifying the tube design.

Yet another advantage resides in providing such dose modulation without additional high speed electronics.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 shows a dose modulated computed tomography imaging apparatus.

Figure 2:
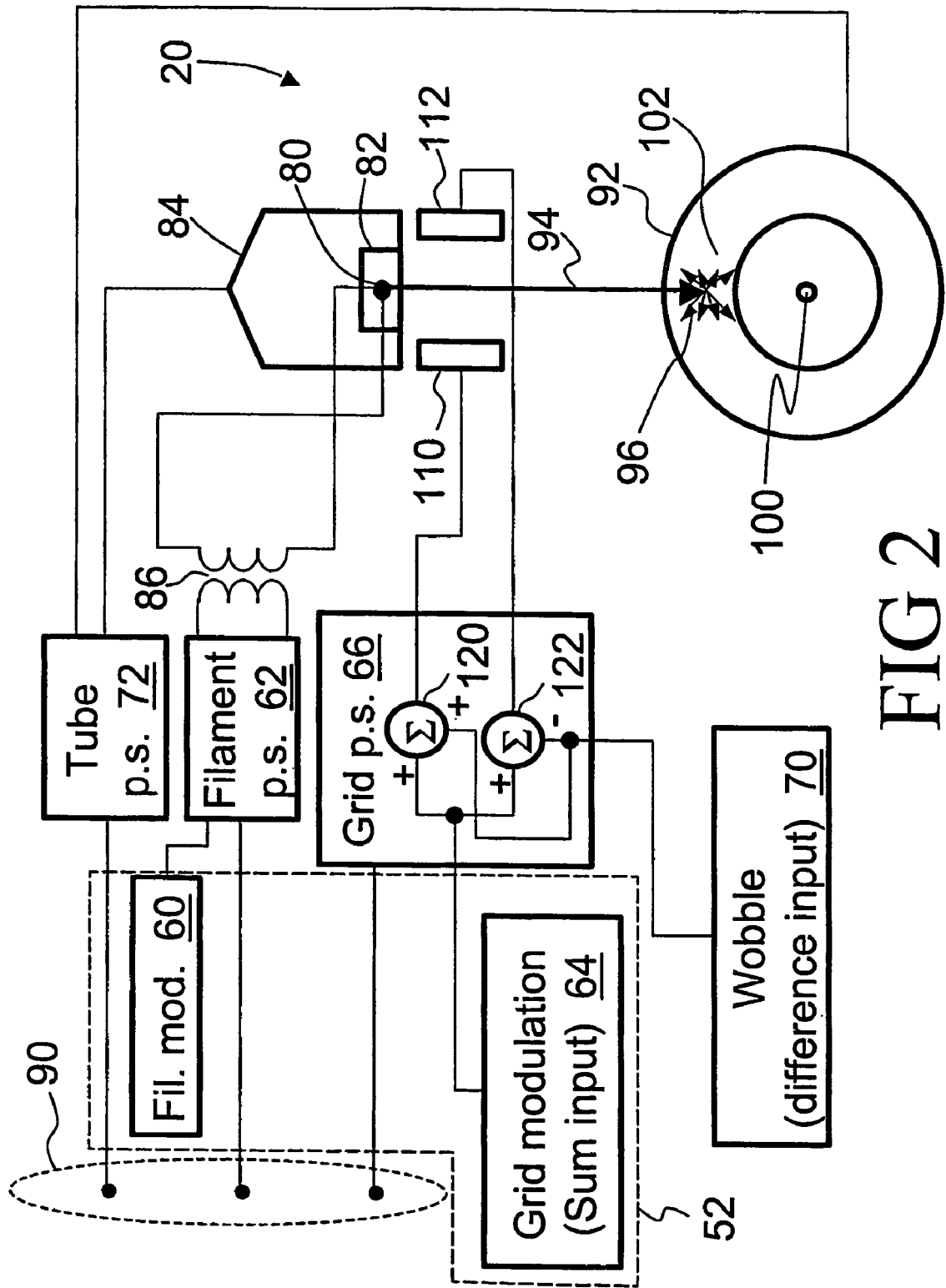

FIG. 2 schematically shows a suitable dose-modulated irradiating system employing electrostatic beam wobbling.

Figure 3:
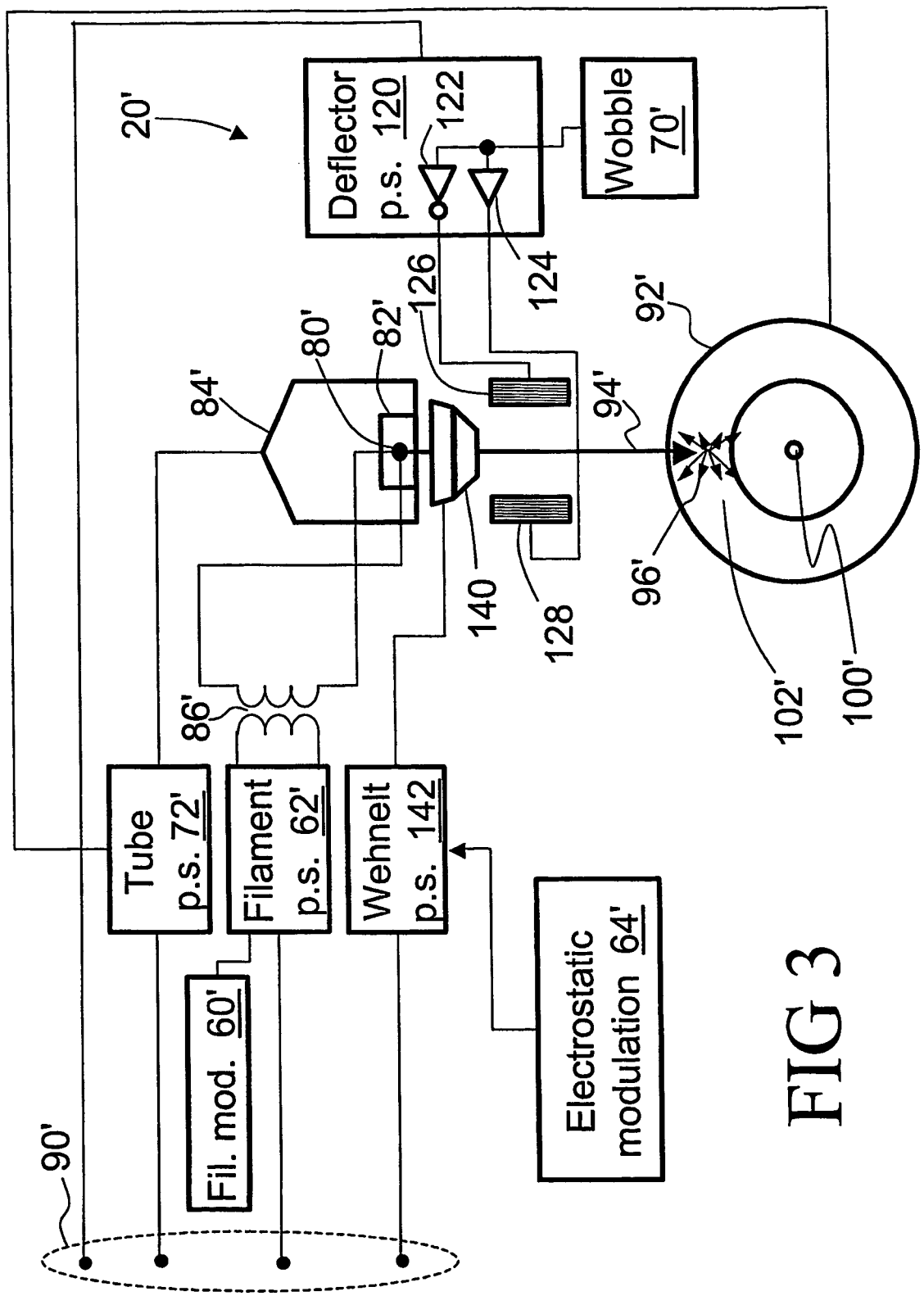

FIG. 3 shows schematically shows a suitable dose-modulated irradiating system employing electromagnetic deflection beam wobbling.

With reference to FIG. 1, a computed tomography imaging scanner 10 includes a subject support 12 for moving a subject such as a medical patient, an item of luggage undergoing a security scan, or the like into or within an examination region 14 defined by a rotating gantry 16. An x-ray tube 20 arranged on the gantry 16 transmits a fan-shaped, wedge-shaped, conically-shaped, or otherwise-shaped x-ray beam into the examination region 14. A two-dimensional x-ray detector 22 disposed on the gantry 16 across the examination region 14 from the x-ray tube 20 measures a spatially-varying intensity of the x-ray beam after the x-ray beam passes through the examination region 14. Typically, the x-ray detector 22 is mounted on the rotating gantry 16. In another suitable arrangement, the detector is arranged circumferentially on a stationary gantry surrounding the rotating gantry. Gantry rotation is controlled by a gantry rotation controller 24.

In helical computed tomography imaging, the gantry 16 rotates simultaneously with a linear motion of the subject support 12 to effect a helical trajectory of the x-ray tube 20 about the examination region 14. In axial computed tomography imaging, the gantry 16 rotates while the subject support 12 remains stationary to effect a circular trajectory of the x-ray tube 20 about the examination region 14. In volumetric axial imaging, the subject support 12 is repeatedly stepped linearly with an axial scan performed for each step to acquire multiple image slices along the axial direction.

Acquired imaging projection data with an index of the apex of the fan or cone and of the trajectory within the fan or cone is transmitted off the gantry 16 and stored in a digital data memory 30. A reconstruction processor 32 reconstructs the acquired projection data, using filtered backprojection or another reconstruction method, to generate a three-dimensional image representation of the subject or of a selected portion thereof, which is stored in an image memory 34. The image representation is rendered or otherwise manipulated by a video processor 36 to produce a human-viewable image that is displayed on a graphical user interface 38 or another display device, printing device, or the like for viewing by an operator. Preferably, the graphical user interface 38 is programmed to interface a radiologist with the computed tomography scanner 10 to allow the radiologist to execute and control computed tomographic imaging sessions.

During imaging, it is advantageous to modulate a x-ray radiation dosage received by the subject. For non-cylindrical objects, it is advantageous to have a higher x-ray beam intensity along the major axis and a lesser intensity along the minor axis. For example, in rapid airport security scanning of luggage the x-ray beam intensity is preferably adjusted depending upon the x-ray absorption characteristics of the scanned luggage. In medical imaging applications, the intensity is preferably adjusted to maintain a constant radiation dose for each axial slice or each helical rotation as an imaging scan passes through regions of the body having differing x-ray absorption densities. Present computed tomography scanners provide rotation rates of about 120-150 rpm, and rotation rates of 180-240 rpm and higher are contemplated in the foreseeable future.

A 120 rpm rotation rate corresponds to an acquisition time of 0.25 seconds for a 180° angular span of data, while a 180 rpm rotation rate corresponds to an acquisition time of 0.167 seconds for 180° of data. Hence, the dose modulation should have a frequency response of about 4 Hz or higher for a 120 rpm gantry rotation rate, and should have a frequency response of about 6 Hz or higher for a 180 rpm gantry rotation rate, to provide dose modulation that tracks the gantry rotation. Higher rotation speeds produce proportionately higher anode milliampere modulation rates. For medical imaging applications, a dose modulation dynamic range of at least about 8:1 to 10:1 is desired. That is, a ratio of a maximum x-ray beam intensity to a minimum x-ray beam intensity during the modulation at all rotation speeds should preferably be at least about 8:1 to 10:1.

To effect dose modulation conforming to these specifications, a dose delivery rate processor 50 integrates the x-ray absorption data over an area of the x-ray detector 22 and inputs a continuously updated dose delivery rate to a dose modulation controller 52. The gantry rotation controller 24 also inputs gantry angular position to the dose modulation controller 52 for optional synchronization of the dose modulation with angular position of the x-ray source 20.

With continuing reference to FIG. 1, the dose modulation controller 52 outputs two synchronized, cooperating dose modulation control signals: a filament modulation signal 60 directed toward an x-ray tube filament power supply 62, and a grid modulation signal 64 directed toward a grid power supply 66. The grid power supply 66 additionally receives a beam wobble input signal 70 which alternates or wobbles a focal spot of the x-ray tube 20 to counteract under-sampling and aliasing in the radial direction. The x-ray tube 20 is driven and controlled by outputs of the filament power supply 62, the grid power supply 66, and a tube power supply 72 which sets the potential between the cathode and the anode.

With continuing reference to FIG. 1 and with further reference to FIG. 2, which schematically shows components of the x-ray tube 20 in cross-section along with associated electronic components, an elongated filament 80, preferably having a wire diameter, for a conventional coiled wire filament, of 8-10 mil, is arranged in a cathode cup 82 of a cathode 84. The filament 80 generates electrons by thermionic emission, field emission, or another mechanism in response to a filament current input delivered by the filament power supply 62. Preferably, an isolation transformer 86 and insulating standoffs (not shown) electrically isolate the filament 80 from other elements of the x-ray tube 20. Typically, the filament current is a pulse-width modulated current with a frequency of about 5 kHz to about 30 kHz and an amplitude ranging from a few hundred milliamperes to a few amperes.

With reference to an electrical common 90, the cathode 84 is typically biased negatively at a bias of around −40 kV to −70 kV and the anode to +40 kV to +70 kV for a bipolarly biased tube. The cathode cup 82 is shaped such that the negative charge defines an electrostatic electric field that collimates electrons generated by the filament 80. The electrons of the electron beam accelerate across the cathode-to-anode gap, which is typically about 2 cm.

In response to the accelerated electron beam 94 striking the anode 92, the anode emits an x-ray beam 96 that passes out of a vacuum volume (not shown) containing the filament 80, the cathode 84, and the anode 92. The anode 92 rotates about an axis 100 and includes an angled circumferential x-ray generating surface 102 that interacts with the electron beam 94 as the anode 92 rotates. The rotation distributes heat across the circumferential surface 102.

With continuing reference to FIGS. 1 and 2, the cathode cup of the x-ray tube 20 further includes first and second grid electrodes 110, 112 arranged on opposite sides of the filament 80 such that the electron beam 94 passes between the grid electrodes 110, 112. The grid electrodes 110, 112 are used to electrostatically modify the electron beam 94.

Specifically, biasing both electrodes 110, 112 more negative narrows a width of the electron beam 94 by electrostatic constriction or aperturing, which affects the focus at the anode. A relatively larger negative sum voltage applied to both electrodes 110, 112 further reduces an intensity of the electron beam 94 at the anode 92 by partial electrostatic pinchoff of the electron beam 94, i.e. reduces the tube current. For a sufficiently large negative bias voltage applied to both electrodes 110, 112 the electron beam 94 can be pinched off entirely.

Additionally, an applied voltage difference, imposed upon the voltage sum, and between the grid electrodes 110, 112, effects a beam deflection.

In another embodiment, the voltage to each grid may be produced as the sum of individual voltages for constriction and deflection, such that the focal spot or spots may be jointly moved essentially tangentially to the rotating anode surface while maintaining correct spot to spot displacement and width.

Additional elements such as one or more additional filaments for redundancy or for achieving different electron beam characteristics and the like, (elements not shown) are also optionally included in the cathode assembly.

With continuing reference to FIGS. 1 and 2, the filament power supply 62 is controlled by the filament modulation signal 60 produced by the dose modulation controller 52. Modulation of the filament current causes modulation of the filament temperature and corresponding modulation of the electron generation rate. This, in turn, modulates the intensity of the electron beam 94 for dose modulation. Changing the filament current does not significantly modify electron trajectories and so does not greatly alter the focus of the electron beam or change the size of the focal spot. However, the filament 80 has a thermal mass which limits the frequency response of this modulation control. For a preferred filament having a 200 micron (8 mil) diameter, modulating the filament current at 4 Hz achieves the frequency response of dose modulation of 4 Hz with corresponding dynamic range of about 2:1 to 3:1. A larger diameter filament has more thermal mass and will typically exhibit a slower frequency response and reduced dynamic range.

In order to obtain dose modulation with better frequency response than that achieved using filament control alone, the dose modulation controller 52 additionally outputs the grid modulation signal 64 directed toward a grid power supply 66. The grid modulation signal 64 is combined with the beam wobble input signal 70 which alternates or wobbles a focal spot of the x-ray tube 20 to produce combined grid electrode biasing potentials.

Specifically, a first summer 120 additively combines the grid modulation signal 64 and the beam wobble input signal 70 to produce a first control signal that controls the electrostatic potential that is applied to the first grid electrode 110. A second summer 122 subtractively combines the grid modulation signal 64 and the beam wobble input signal 70 to produce a second control signal that controls the electrostatic potential that is applied to the second grid electrode 112. The grid electrodes therefore receive a differential potential controlled by the beam wobble input signal 70 which controls the beam wobble, and a superimposed sum potential controlled by the grid modulation signal 64.

The frequency response of analog dose modulation performed by modulating the sum grid potential is limited by a frequency response of the grid power supply 66. Existing grid power supplies used for electrostatic beam wobble alternately position the focal spot between two tightly controlled locations using a differential potential applied to the grid electrodes 110, 112. The beam is stepped between the focal spots in response to a square voltage pulse beam wobble input signal 70, at around 2-4 kHz for a 120 rpm gantry rotation and 2000 projection views per rotation.

The harmonic content of the square-wave beam wobble input signal 70 leads to high bandwidth requirements for the grid power supply 66, which is usually a switching power supply. Such power supplies today typically exhibit a limited analog frequency response (as opposed to a power amplifier, which would have a much higher bandwidth but would also be more costly) such that modulation of the grid potentials alone does not achieve dose modulation at the desired frequency response of about 4 Hz to 6 Hz or higher with a dose modulation dynamic range of about 8:1 to 10:1.

To achieve the desired dose modulation frequency response and dynamic range, the dose modulation controller 52 S cooperatively controls the grid modulation signal 64 and the filament modulation signal 60 to cascade the grid electrode dose modulation and the filament current dose modulation. For a 4-6 Hz modulation frequency, a product of the cascaded grid and filament dose modulations provides the desired 8:1 to 10:1 dynamic modulation range. Moreover, dynamic range can be traded off for higher dose modulation frequency.

A further benefit of combined grid and filament dose modulation is improved focus of the electron beam 94 throughout the dynamic modulation range. The x-ray tube 20 is designed to operate with a small spot size at relatively high output power. Combined grid and filament dose modulation reduces the output power by cooperatively reducing the filament current and increasing the sum potential on the grid electrodes 110, 112. Beam narrowing due to higher sum grid potentials, results in improved electron beam spot size on the anode 92 during dose modulation and consequently improved spatial definition of the x-ray beam 96 throughout the dynamic modulation range.

In FIG. 2, the first and second summers 120, 122 are integrated into the grid power supply 66. However, it is also contemplated to arrange these elements outside of the grid power supply, and supply the summer outputs as inputs to the grid power supply. This alternate arrangement facilitates retrofitting a computed tomography imaging system which include a grid power supply for beam wobble with dose modulation capability that uses cascaded filament current and grid sum potential modulations.

Moreover, it will be recognized that the cascaded dose modulation can be performed with or without concurrent focus switching. That is, the beam wobble input signal 70 can be turned off or omitted entirely from the computed tomography imaging system while retaining the cascaded dose modulation aspect.

With reference to FIG. 1, the above-described beam modulation can be employed in a variety of ways. In one suitable dose modulated imaging process, the dose modulation controller 52 integrates the dose delivery rate received from the dose delivery rate processor 50 over a 360° revolution of the gantry 16 corresponding to an axial slice or one turn of a helical trajectory. Based on the integrated dose delivered to the subject over 360°, the dose modulation controller 52 adjusts the sum potential on the grid electrodes 110, 112 and the current through the filament 80 for the next 360° revolution to maintain a generally constant radiation dose delivered for each slice or helical revolution. As the imaging progresses axially between regions of the subject having differing absorption characteristics, the x-ray beam is modulated to maintain a generally constant x-ray absorption rate in the subject.

In another suitable dose modulated imaging process, the dose modulation controller 52 continuously adjusts the sum potential on the grid electrodes 110, 112 and the current through the filament 80 to maintain a generally constant dose delivery rate as reported by the dose delivery rate processor 50. This process can adjust the radiation delivery rate during acquisition of projection data for a single slice, and is particularly suitable for large-pitch helical scanning in which a substantial axial distance is sampled during each 360° gantry rotation.

The x-ray tube 20 uses electrostatic beam deflection to implement beam wobble. Hence, the grid electrodes 110, 112 are used for the electrostatic beam wobble and are additionally used for electrostatically dose modulating through the applied sum potential. However, in some existing x-ray tubes an electrostatic grid is not used. Rather, the electrostatic grid is replaced by an electromagnetic beam deflector.

With reference to FIG. 3, an x-ray tube 20' uses separate electromagnetic beam deflection for wobble and electrostatic electron beam constriction or aperturing for dose modulation. FIG. 3 schematically shows components of the x-ray tube 20' in cross-section along with associated electronic components. Components in FIG. 3 that generally correspond with components of FIG. 2 are indicated by corresponding primed reference numbers.

Specifically, the x-ray tube 20' includes a filament 80', a cathode 84' with a cathode cup 82', and an anode 92' with a rotational axis 100' and an angled circumferential x-ray generating surface 102'. These components generally correspond to the filament 80, cathode 84, cathode cup 82, anode 92, rotational axis 100, and surface 102 of the x-ray tube 20. Moreover, x-ray tube control hardware including a filament power supply 62' with an isolation transformer 86' and a tube power supply 72' operate similarly to corresponding elements 62, 86, 72 of FIG. 2 in applying bias potentials relative to a common 90' and generating an electron beam 94' and an x-ray beam 96'. A beam wobble input signal 70' and a filament current modulation control signal 60' correspond to the analogous input signals 70, 60 of FIGS. 1 and 2.

The x-ray tube 20' employs electromagnetic beam deflection rather than the electrostatic beam deflection employed by the x-ray tube 20. Specifically, the beam wobble input signal 70' is input into a deflector power supply 120. Inverting and non-inverting paths 122, 124 generate power for driving electromagnets 126, 128 based on the input signal 70' to steer the electron beam 94' between two wobble position focal spots. Two electromagnets 126, 128 are shown. However, a single solenoidal electromagnet can also be employed.

Unlike the electrostatic grid electrodes 110, 112 of the x-ray tube 20, the electromagnets 126, 128 of the x-ray tube 20' cannot constrict the electron beam to effect a dose modulation. Rather, separate electrostatic beam constriction elements are included in the tube 20'.

A Wehnelt cylinder 140 is driven by a Wehnelt power supply 142. The grid modulation input signal 64 of FIGS. 1 and 2 is replaced by an analogous electrostatic modulation signal 64' which is input to the Wehnelt power supply 142. A negative potential applied to the Wehnelt cylinder 140 effects a reduction in an intensity of the electron beam 94' at the anode 92' by partial electrostatic pinchoff of the electron beam 94'. For a sufficiently large negative potential applied to the Wehnelt cylinder 140 the electron beam 94' can be pinched off entirely. The Wehnelt cylinder 140 is biased negatively with respect to the cathode 84', typically in a range of zero volts to about 3 kV more negative than the cathode 84'.

The Wehnelt cylinder 140 performs electrostatic beam modulation based on the electrostatic modulation signal 64' in substantially the same manner that the grid electrodes 110, 112 of the x-ray tube 20 perform electrostatic beam modulation based on the sum electrostatic potential 64. Electrostatic dose modulation via the Wehnelt cylinder 140 is suitably combined with modulation of current in the filament 80' to provide cascaded electrostatic and filament current controlled dose modulation. Benefits of this cascaded dose modulation described with reference to the x-ray tube 20 apply also to the x-ray tube 20', such as improved dynamic range of the radiation modulation and improved spatial definition of the x-ray beam over the dynamic modulation range. Moreover, the x-ray tube 20' optionally includes additional elements such as fluid passages for active cooling, one or more additional filaments for redundancy or for achieving different electron beam characteristics, and the like (elements not shown).

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A dose-modulated irradiating system for an x-ray tube with a cathode including a filament that generates electrons which are focused into a beam and an anode that generates x-rays responsive to the electron beam, the dose-modulated irradiating system further including:
   at least one electrostatic control electrode arranged to electrostatically reduce an intensity of the electron beam; and
   a biasing means for applying a time-varying electrical bias to the electrostatic control electrode to vary the intensity of the electron beam.

2. The dose-modulated irradiating system as set forth in claim 1, wherein the electrostatic control electrode includes an electrostatic grid with grid electrodes arranged for steering the electron beam responsive to an applied differential potential.

3. The dose-modulated irradiating system as set forth in claim 1, further including:
   a current-modulating means for applying a time-varying filament current through the filament; and
   a control means for controlling the biasing means and the current-modulating means to produce a selected time varying intensity of the electron beam.

4. The dose-modulated irradiating system as set forth in claim 3, wherein the control means concurrently invokes the biasing means and the current-modulating means to vary the filament current simultaneous with the time-varying electrical bias on the electrostatic control electrode cooperatively producing the selected time varying intensity of the electron beam.

5. The dose-modulated irradiating system as set forth in claim 1, further including:
   a rotating gantry on which the x-ray tube is disposed, the rotating gantry defining an examination region into which the x-ray tube transmits an x-ray beam;
   a two-dimensional x-ray detector arranged across the examination region from the x-ray tube that measures a spatially-varying intensity of the x-ray beam after the x-ray beam passes through the examination region; and
   a processor that reconstructs a computed tomographic image of an imaging subject disposed in the examination region based on the spatially-varying intensity of the x-ray beam measured by the x-ray detector at a plurality of positions of the x-ray source.

6. The dose-modulated irradiating system as set forth in claim 5, wherein the electrostatic control electrode includes an electrostatic grid with grid electrodes arranged about the filament, the dose-modulated irradiating system further including:

a second biasing means for applying a switched difference electrical bias to the grid electrodes to wobble the electron beam between alternating focal spots.

7. The dose-modulated irradiating system as set forth in claim 5, further including:
a filament current controller that applies a time-varying filament current through the filament; and
a controller that controls the biasing means and the filament current controller to produce a selected time varying radiation dosage applied to the imaging subject.

8. The dose-modulated irradiating system as set forth in claim 5, further including:
a filament current controller that applies a time-varying filament current through the filament;
a feedback element that computes a control signal corresponding to a rate of radiation delivered to the imaging subject based on the spatially-varying intensity of the x-ray beam measured by the x-ray detector; and
a controller that controls the biasing means and the filament current controller to produce a substantially constant control signal.

9. The dose-modulated irradiating system as set forth in claim 1, wherein the electrostatic control electrode includes paired grid electrodes arranged on opposite sides of the filament, and the electrostatic control modulator additionally applies a switched differential electrical bias component applied to the grid electrodes that causes a wobbling of the electron beam.

10. The dose-modulated irradiating system as set forth in claim 1, wherein the electrostatic control electrode includes a Wehnelt cylinder.

11. The dose-modulated irradiating system as set forth in claim 10, further including:
an electromagnetic deflector that selectively deflects the electron beam.

12. The dose-modulated irradiating system as set forth in claim 1, further including:
a computed tomography imaging scanner on which the cathode, the anode, and the electrostatic control electrode are mounted as a unitary x-ray tube unit.

13. The dose-modulated irradiating system as set forth in claim 1, wherein the biasing means applies the time-varying electrical bias to the electrostatic control electrode to vary the intensity of the electron beam between at least a first intensity and a second intensity, wherein the first intensity is greater than the second intensity, and the second intensity is a positive, non-zero intensity.

14. The dose-modulated irradiating system as set forth in claim 1, wherein the time-varying electrical bias includes a negative sum voltage, wherein increasing the negative sum voltage reduces the intensity of the electron beam.

15. The dose-modulated irradiating system as set forth in claim 14, wherein the negative sum voltage is a summation of two or more individual voltages.

16. The dose-modulated irradiating system as set forth in claim 1, wherein the time-varying electrical bias causes the electrostatic control electrode to partially pinch off the electron, thereby reducing the intensity of the electron beam when varying the intensity of the electron beam.

17. A method for dose-modulating an output of an x-ray tube that includes a cathode having a filament that generates electrons which are focused into a beam, an anode that generates x-rays responsive to the electron beam, and an electrostatic control electrode that electrostatically adjusts an intensity of the electron beam, the method including:
applying a time-varying electrical bias to the electrostatic control electrode to produce a first time-varying intensity modulation of the electron beam.

18. The method as set forth in claim 17, further including:
simultaneously with the applying of a time varying electrical bias, applying a time-varying filament current to produce a second time-varying intensity modulation of the electron beam, the first and second time-varying intensity modulations cascading to enhance a dynamic range over which the intensity of the electron beam is modulated.

19. The method as set forth in claim 18, wherein a ratio of a maximum x-ray beam intensity to a minimum x-ray beam intensity during the time varying intensity modulation is at least 8:1.

20. The method as set forth in claim 17, further including:
synchronizing the applying of the time-varying electrical bias with a rotation of a rotating gantry of a computed tomography apparatus on which the x-ray tube is arranged.

21. The method as set forth in claim 17, wherein the x-ray tube is a radiation source component of a computed tomography imaging scanner, the method further including:
imaging an imaging subject using the computed tomography imaging scanner;
during the imaging, measuring x-ray intensities using an x-ray detector component of the computed tomography imaging scanner;
estimating a temporally varying radiation dose delivery rate of x-ray radiation delivered to the imaging subject during the imaging based on the measured x-ray intensities; and
controlling the applying of the time-varying electrical bias during the imaging based on the estimated temporally varying radiation dose delivery rate.

22. The method as set forth in claim 21, wherein the controlling step controls the applying of the time-varying electrical bias to maintain a selected generally constant radiation dose delivery rate.

23. The method as set forth in claim 17, wherein the x-ray tube is a radiation source component of a computed tomography imaging scanner, the method further including:
imaging an imaging subject using the computed tomography imaging scanner, the applying of the time-varying electrical bias to the electrostatic control electrode being performed during the imaging to provide modulation of a radiation delivery rate.

24. The method as set forth in claim 23, further including:
controlling a filament current of the cathode to produce a second time-varying intensity modulation of the electron beam, the first and second time-varying intensity modulations of the electron beam being temporally coordinated to provide the modulation of the radiation delivery rate.

25. The method as set forth in claim 24, wherein the electrostatic control electrode includes an electrostatic grid with grid electrodes arranged about the filament, the method further including:
applying a switched differential electrical bias to the grid electrodes concurrently with the applying of the time-varying electrical bias to wobble the electron beam.

26. The method as set forth in claim 17, wherein the time varying electrical bias applied to the electrostatic control electrode is an analog time varying electrical bias.

* * * * *